United States Patent [19]
Karube et al.

[11] Patent Number: 4,975,175
[45] Date of Patent: Dec. 4, 1990

[54] MINIATURIZED OXYGEN ELECTRODE AND MINIATURIZED BIOSENSOR AND PRODUCTION PROCESS THEREOF

[75] Inventors: Isao Karube, 2467-11, Arima, Miyamae-ku, Kawasaki-shi, Kanagawa 213; Hiroaki Suzuki, Sagamihara, both of Japan

[73] Assignees: Isao Karube, Kawasaki; Fujitsu Limited, Kanagawa, both of Japan

[21] Appl. No.: 366,365

[22] Filed: Jun. 15, 1989

Related U.S. Application Data

[63] Continuation of Ser. No. 174,501, Mar. 28, 1988, abandoned.

[30] Foreign Application Priority Data

| Mar. 27, 1987 | [JP] | Japan | 62-071739 |
| Mar. 27, 1987 | [JP] | Japan | 62-071738 |
| Jun. 15, 1987 | [JP] | Japan | 62-148221 |
| Mar. 2, 1988 | [JP] | Japan | 63-47363 |
| Mar. 3, 1988 | [JP] | Japan | 63-48708 |

[51] Int. Cl.⁵ .......................................... G01N 27/404
[52] U.S. Cl. ............................ 204/403; 29/592 R; 128/635; 204/414; 204/415; 435/817; 437/228
[58] Field of Search ............... 204/403, 414, 415, 1 E, 204/1 P; 128/635; 435/817; 29/592 R

[56] References Cited

U.S. PATENT DOCUMENTS

| 4,062,750 | 12/1977 | Butler | 204/15 X |
| 4,505,799 | 3/1985 | Baxter | 204/416 |
| 4,874,500 | 10/1989 | Madou et al. | 204/412 |

FOREIGN PATENT DOCUMENTS

2426904 12/1979 France.

Primary Examiner—G. L. Kaplan
Attorney, Agent, or Firm—Staas & Halsey

[57] ABSTRACT

Miniaturized Clark-type oxygen electrodes includes a substrate having at least one recess groove formed on a surface thereof for receiving an electrolyte solution, and two electrodes acting as a cathode and an anode formed through an insulating layer on the surface of the substrate. Each of the electrodes is at least partially disposed in a bottom area of the recess. A solid or semi-solid, porous, electrolyte solution-containing material fills the recess, and an oxygen gas-permeable membrane covers and seals the recess and porous material received therein. Miniaturized biosensors are made using the oxygen electrode as a transducer. The oxygen electrodes and biosensors, which are extremely accurate, can be mass-produced and can be widely used in various fields such as clinical analysis, industrial processing, and in the determination of environmental conditions. The biosensors can be particularly used in clinical diagnosis and in monitoring devices for both in vivo and in vitro measurements.

36 Claims, 18 Drawing Sheets

MINIATURIZED OXYGEN ELECTRODE AND MINIATURIZED BIOSENSOR AND PRODUCTION PROCESS THEREOF

BACKGROUND OF THE INVENTION

1. Field of the Invention

The present invention relates to miniaturized oxygen electrodes, i.e., Clark-type "micro-" oxygen electrodes, and processes for the production thereof using a semiconductor fabrication technology. The oxygen electrodes can be advantageously used for determining a concentration of oxygen dissolved in a specific solution or other mediums. For example, these electrodes can be used as a device for measuring BOD (Biological Oxygen Demand) in water in the field of water control and the like. Further, in fermentation industries, such electrodes can be used to determine the concentration of dissolved oxygen in a fermentation tank, to realize an effective alcohol fermentation therein. Furthermore, such electrodes can be used as a transducer to produce enzyme electrodes or biosensors for, for example, sugars and vitamins. As an example, such a biosensor, when combined with the enzyme: GOD (glucose oxidase) as a catalyst, can act as a glucose sensor. This is because glucose ($C_6H_6O_{12}$) is oxidized to gluconolactone ($C_6H_{10}O_6$), when reacted with dissolved oxygen in the presence of the catalyst BOD, and as a result of this oxidation reaction, the amount of the dissolved oxygen diffused into a sensing cell of the oxygen electrode is reduced. Based on this reduction of the dissolved oxygen, a concentration of glucose can be exactly determined. The micro-oxygen electrodes of the present invention can be widely utilized in the fields of, for example, clinical analysis, industrial processing, and environmental conditioning.

The present invention also relates to miniaturized biosensors i.e., "micro-" biosensors. These micro-biosensors also can be widely used in various fields, similar to the micro-oxygen electrodes, since these sensors are extremely small and are disposable, if desired, due to low production costs. For example, in the medical and clinical fields, the micro-biosensors can be combined with a catheter to carry out in vivo measurements.

2. Description of the Related Art

As well known in the art, there are two groups of Clark-type oxygen electrodes. Namely, polarographic electrodes in which a determination of the oxygen concentration is carried out by applying a predetermined voltage between the electrodes, and galvanic electrodes wherein the oxygen determination is made by utilizing spontaneously proceeding reactions. These oxygen electrodes have similar structures, but are distinguishable by the materials used for the electrode structure. If both the cathodes and the anodes are made from chemically stable noble metals such as gold and platinum, they are classified as polarographic oxygen electrodes, but if the anodes are made from metals having a higher tendency to induce chemical reactions than the noble metals, for example, lead and silver, they are classified as galvanic oxygen electrodes.

A typical example of the prior art Clark-type oxygen electrodes is illustrated in FIG. 1. The illustrated electrode is a galvanic oxygen electrode and is known and conveniently used as an oximeter for measuring dissolved oxygen. The electrode consists of an open-ended glass container 21, an oxygen gas-permeable membrane 25 such as TEFLON (polytetrafluoroethylene) covering a bottom portion of the container 21 and sealed with an O-ring 22, an electrolyte solution 24 such as 1 M KOH retained in the container 21 and two electrodes, i.e., a working electrode (cathode) 23A made of e.g., platinum, and a counter electrode (anode) 23B made of, e.g., lead. Details concerning the structure and determination of the oxygen concentration of the Clark-type electrode can be found in many references, such as S. Suzuki, "Ion electrodes and enzyme electrodes", 1981, Kodansha, Tokyo.

The prior art Clark-type oxygen electrodes, however, are not suitable for mass-production because they must be manually fabricated using a glass working technology, and, are thus very expensive. They are also unacceptably large for many usages; e.g., they cannot be used for in vivo measurements of oxygen concentration. Moreover for technical reasons, they cannot be miniaturized to a size smaller than that of, for example, a pencil.

New Clark-type oxygen electrodes fabricated by using a semiconductor fabrication technology in which the drawbacks of the glass-made electrodes are avoided, have been developed by Prof. T. Moriizumi et al. of the Tokyo Institute of Technology. As reported in, for example, Y. Miyahara, F. Matsu, S. Shiokawa, T. Moriizumi, H. Matsuoka, I. Karube and S. Suzuki, Proc. of the 3rd Sensor Symp., (Inst. Electr. Eng. Jap.), 21 (1983), the miniaturized and integrated oxygen electrodes are produced by anisotropically etching a silicon wafer to form V-shaped grooves on a surface of the wafer, depositing the Au cathode and Ag anode on a selected surface of the wafer, pouring an alkaline solution of electrolyte into the grooves, and finally, covering the electrolyte solution-containing grooves with an oxygen-permeable membrane, made of, e.g., TEFLON. The thus-produced oxygen electrode is shown as a cross-sectional view of the sensing site of the electrode in FIG. 2 of the accompanying drawings.

In FIG. 2, the oxygen electrode consists of a silicon chip 31 having a V-shaped groove formed on a surface thereof. Two silver (Ag) electrodes 32 and a gold (Au) electrode 33 are deposited on the V-grooves and are covered with a TEFLON membrane 30. A space formed between the V-grooves and the membrane 30 is filled with an aqueous solution of an electrolyte 36 such as NaOH or NaCl. The resulting sensing site of the electrode is placed in contact with another silicon chip 34, and sealing using an epoxy adhesive 38 is carried out. Reference numerals 35 and 37 each represent a silicon oxide coating obtained through a thermal oxidation of the exposed silicon chips 34 and 31, respectively. This oxygen electrode has many advantages, for example, extremely small size, reduction of the necessary amount of samples to be tested, high reliability and precision, and mass-production capability, compared with the above glass electrodes, but suffer from several disadvantages. For example, since the TEFLON coating used as the gas-permeable membrane will not adhere to many materials, it is necessary to use an additional adhesive means to assist the adhesion of this coating. Further, the structure of the electrode is relatively complicated, and it is desirable to provide a more simplified electrode structure.

The oxygen electrode of Japanese Unexamined Patent Publication (Kokai) No. 60-146145 was invented to solve the problems of the oxygen electrode described above with reference to FIG. 2. From FIG. 3 of the accompanying drawings, it can be understood that this electrode is similar to that of FIG. 2, except that an anode electrode was formed on a silicon (Si) substrate, and a cathode electrode was formed on an electrolyte-facing surface of the gas-permeable membrane, respectively. In FIG. 3, 30 is a gas-permeable membrane made of, e.g., TEFLON, 31 a lower Si wafer, 32 a Cr-Ag anode, 33 an Au cathode, 34 an upper Si wafer, 35 an $SiO_2$ layer, 36 an electrolyte solution such as 1 M KOH, 37 an $SiO_2$ layer, and 38 an epoxy sealing agent. According to this electrode, the steps necessary to produce the electrode can be reduced and a response speed of the electrode can be increased.

Also, the oxygen electrode of Japanese Unexamined Patent Publication (Kokai) No. 61-30756 was invented to solve the problems of the electrode of FIG. 2. The oxidation electrode of this reference, as illustrated in FIG. 4, has a structure similar to that of FIG. 2 and comprises a silicon chip 31, an Ag anode 32, an Au cathode 33, and an $SiO_2$ layer 37. Recesses on the chip 31 contain an electrolyte solution 36 such as NaOH or NaCl. An upper surface of the chip 31 including recesses is covered with an organic coating 30 such as polyamide. In order to adhere the coating 30 to the silicon chip 31 and the cathode 33, an interlayer 39 such as a polyaminosiloxane coating is used. The organic coating 30 and the interlayer 39, make it possible to simplify the complicated fabrication steps in the production of the miniaturized and integrated oxygen electrodes.

In the production of the prior art miniaturized oxygen electrodes discussed above, the anisotropic etching technology was used to form microrecesses on the silicon wafer, into which the electrolyte solution is then poured. However, since this technology makes the process complex and cumbersome, and requires the use of hydrofluoric acid which is dangerous to operators, it is desirable to develop an improved production process of the miniaturized oxygen electrodes without using the conventional anisotropic etching technology.

Recently, such a production process was invented by researchers at Fujitsu Limited (see Japanese Unexamined Patent Publication (Kokai) No. 62-39755). As apparent from FIG. 5 of the accompanying drawings, the production process comprises patterning an Ag anode 42 on a surface of a glass substrate 41, coating a photosensitive resin 44 on a surface of the substrate 41, selectively etching the resin coating 44 to form a cell 45 and an output terminal 46 of the anode 42, and then patterning an Au cathode 43 on the surface of the resin coating 44. The electrolyte solution is poured through an injection port 47 into the cell 45. This production process makes it possible to safely and easily produce miniaturized oxygen electrodes without disconnection of the electrodes, and in addition, the anisotropic etching step can be omitted.

Generally speaking, the prior art oxygen electrodes are considered to be satisfactory, since they are compact and have a simple structure. However, undesirably, the electrolyte solution used tends to have an adverse effect on the resulting electrode, since it is in the form of liquid. Further, the gas-permeable membrane, particularly the coating of fluoropolymers, causes problems due to poor adhesion properties. It is, therefore, desired to provide a further improved miniaturized oxygen electrode and a production process thereof, as well as an improved miniaturized biosensor.

SUMMARY OF THE INVENTION

According to the present invention, there is provided a miniaturized oxygen electrode which comprises a substrate having at least one recess for reserving an electrolyte solution formed on a surface thereof, two electrodes acting as a cathode and an anode formed through an insulating layer on the surface of the substrate, each of which electrodes is at least partly extended toward a bottom area of the recess, a solid or semi-solid, porous, electrolyte solution-containing material filled in the recess, and an oxygen gas-permeable membrane covering and sealing the recess and porous material reserved therein.

The miniaturized oxygen electrodes of the present invention are preferably in the form of rectangular plates, and generally, have dimensions on the order of millimeters, i.e., a length of about 5 to 20 mm, a width of about 1 to 5 mm and a thickness of less than 1 mm. Note, although these electrodes do not have dimensions on the order of microns, they are usually referred to as micro-oxygen electrodes. Namely, the term micro- used herein is intended to mean that the micro-oxygen electrodes or microbiosensors of the present invention are microminiature electrodes or sensors.

The material of the substrate used herein is not restricted, insofar as a desired pattern of grooves or recesses can be easily and accurately formed on a surface of the selected material by photolithographic and anisotropic etching. The substrate material is preferably a semiconductor material conventionally used in the field of production of semiconductor devices, such as silicon, gallium-arsenic, sapphire, and the like. Most preferably, silicon is used as the substrate material, since an insulating layer of silicon oxide, which is essential to the micro-oxygen electrodes of the present invention, can be subsequently formed by a thermal oxidation of the silicon substrate.

The electrolyte solution-containing material used in the present invention is not used as a liquid, but in a solid or semi-solid form. Namely, the electrolyte solution is used after impregnation thereof with a solid or semi-solid porous material. The electrolyte solution-carrying material is reserved in the recesses formed on the substrates.

The electrolyte solution-carrying materials may have any desired form. For example, the electrolyte solution may be impregnated into fine pores of a porous glass or other porous materials. Further, the porous material may be an agarose gel having the electrolyte solution entrapped therein, or may be a polymeric gel of photopolymerizable monomers having the electrolyte solution entrapped therein. The photopolymerizable monomers are preferably acrylamide. Furthermore, the porous material may be a metal alkoxide gel having the electrolyte solution entrapped therein.

In the selection and preparation of the electrolyte solution-carrying material, the electrolyte ions must be easily movable in the selected material, variations in the volume of the material as a function of the evaporation of water must be negligibly small, the material must have a high mechanical strength, and the material must have a good adhesion to both the substrate and the gas-permeable membrane. Further, for mass-production using semiconductor fabrication technology, the material is preferably selectively etched or laminated.

As the electrolyte solution to be carried by the porous material, any substances conventionally used as the electrolyte in the field can be used. Typical examples of such electrolytes include sodium sulfate ($Na_2SO_4$), potassium chloride (KCl), potassium hydroxide (KOH), and the like. The selection of such electrolytes will depend on the type of the desired oxygen electrodes, and particularly, the anodes and cathodes used therein.

Two electrodes can be preferably formed on the surface of the substrate by a conventional film-forming method such as vacuum deposition, sputtering and the like. The materials used for these electrodes depend upon the type of oxygen electrodes required. Namely, such materials can be widely varied depending on whether a polarographic electrode or a galvanic oxygen electrode is desired. For example, in the production of the polarographic oxygen electrodes, both electrodes can be made from gold or platinum and, during operation, a predetermined voltage is applied between these electrodes. The electrolyte solution used in this type of electrode is preferably an aqueous and neutral solution such as an aqueous solution of 0.1 M KCl, since these neutral electrolytes will not substantially adhere to the underlying substrate or insulating layer. Moreover, when gold, platinum or similar electrodes are used as the cathode, silver/silver chloride, lead, silver, and similar electrodes are used as the anode and an aqueous and alkaline solution such as an aqueous solution of 1 M KOH is used as the electrolyte solution, galvanic oxygen electrodes can be produced.

Since the electrolyte-carrying material used is a solid or semi-solid, it is possible to apply an oxygen gas-permeable membrane to the surface of the substrate without difficulty. Such a membrane can be formed in situ, namely, by coating a solution of the membrane-forming material on the substrate surface and then hardening the coating. This formation of the gas-permeable membrane is convenient, because it becomes unnecessary to use commercial gas-permeable films or to fix the films to the surface of the substrate using an adhesive or other means. The resulting gas-permeable membrane is hydrophobic and impermeable to the electrolyte solution and test solution.

As apparent from the above, the gas-permeable membrane-forming material is in the form of an aqueous solution or another liquid state and, therefore, can be easily applied to the substrate surface by a conventional coating method such as dip coating and spin coating. Also, the membrane-forming material ensures a strong connection between the resulting membrane and the substrate, insulating layer or electrodes. Suitable membrane-forming materials include silicone resins, photoresist and similar materials. Among the photoresist materials, negative-working photoresist materials are preferably used as the membrane-forming material, because they are highly hydrophobic, and thus easily repel the aqueous electrolyte solution, fluoropolymers such as TEFLON should not be used due to an insufficient adhesion force thereof, although they exhibit an excellent oxygen permeability.

According to the present invention, there is also provided a process for the production of miniaturized oxygen electrodes which comprises the steps of:
forming at least one recessed groove on a substrate by photolithographic and anisotropic etching,
forming an insulating layer on the surface of the recess-grooved substrate,
forming two electrodes on the surface of the insulating layer in such manner that the electrodes are at least partly extended toward a bottom area of the recess,
filling the recess with a solid or semi-solid, porous, electrolyte solution-containing material, and
covering and sealing the recess containing the porous material with an oxygen gas-permeable membrane.

In the practice of the present invention, a heated solution of gel-forming substances such as agarose, containing the electrolyte solution may be poured into the recess and left to stand to form an agarose gel having the electrolyte solution entrapped therein.

Further, a solution of photopolymerizable monomers containing the electrolyte solution may be poured into the recess and radiations capable of inducing a polymerization of the monomers irradiated onto the substrate to form a polymeric gel having the electrolyte solution entrapped therein. The photopolymerizable monomers used herein are preferably acrylamide and, therefore, UV rays are used as an exposure source to cause polymerization of acrylamide. In this formation of an electrolyte-carrying gel, in order to accelerate the filling of the recesses with the gel, after the formation of the electrodes, the surface of the substrate, exclusive of the recess portion, may be entirely coated with a hydrophobic photoresist material, the masked substrate dipped in an aqueous solution of photopolymerizable monomers containing the electrolyte solution, and the substrate containing the aqueous solution of monomers in the recess exposed to radiations capable of inducing polymerization of the monomers to form a polymeric gel having the electrolyte solution entrapped therein.

The above dipping method is suitable for the mass-production of oxygen electrodes, and, when the substrate is exposed to the radiations, the exposure should be made after the recess formed thereon has been covered and closed with an evaporation-preventing means through which the radiations can pass. This is because the covering means applied, such as a transparent plate or film, can effectively prevent an undesirable evaporation of water from the electrolyte-containing recesses during gelation. This is based on findings that, if the size of the recesses for the electrolyte solution is reduced, a ratio of the surface area of the recess to the volume thereof is remarkably increased and, therefore, the evaporation of water from the electrolyte solution is accelerated, and that such evaporation is further accelerated when heat is applied to the electrolyte solution during the gelation of the starting monomers. Exposure of the substrate in an atmosphere saturated with water vapour should be avoided, because the electrolyte solution will absorb water from the atmosphere during the gelation and, finally, will expand to twice or more the original volume.

According to the present invention, in order to form an electrolyte solution-carrying gel, a solution of metal alkoxide (for example, tetraethoxysilane) containing the electrolyte solution may be poured into the recess and subjected to a sol-gel process to form a metal alkoxide gel having the electrolyte solution entrapped therein, or after formation of the electrodes, the surface of the substrate, exclusive of the recess portion, may be entirely coated with a hydrophobic photoresist material, the masked substrate dipped in an aqueous solution of metal alkoxide containing the electrolyte solution, and the substrate containing the aqueous solution of metal alkoxide in the recess subjected to a sol-gel process to form a gel of metal alkoxide having the electrolyte solution entrapped therein.

The above method for forming an electrolyte solution-carrying material or gel is based on the sol-gel method conventionally used in the production of glass. This method is particularly useful when the resulting oxygen electrodes are to be used for in vivo measurements, because the gel produced according to this method or starting materials thereof has no toxicity to the human body. Although the polyacrylamide gel described above also does not have toxicity, acrylamide, i.e., the starting material thereof, is toxic to the human body. The acrylamide monomer must be completely consumed during gelation and a small amount of the monomer remaining in the recesses must be sealed with the overlaying gas-permeable membrane.

Also, according to the present invention, there is provided a miniaturized biosensor which substantially consists of an oxygen electrode comprising a substrate having at least one recess groove formed on a surface thereof for reserving an electrolyte solution, two electrodes acting as a cathode and an anode formed through an insulating layer on the surface of the substrate, each of which electrodes is at least partly extended toward a bottom area of the recess, a solid or semi-solid, porous, electrolyte solution-containing material filling the recess, an oxygen gas-permeable membrane covering and sealing the recess and porous material reserved therein; and an immobilized biological substance which can catalyze the oxidation of biochemical organic compounds positioned on a sensitive site of the oxygen electrode.

In the microbiosensor according to the present invention, the biological substance is preferably an enzyme or a mixture of two or more enzymes, or microorganisms or a combination of two or more enzymes and microorganisms.

The microbiosensor of the present invention can be applied to various sensors, depending upon the specific biological substances used as a receptor. The microbiosensor is preferably used as a glucose sensor, as described hereinafter in detail.

DESCRIPTION OF THE PREFERRED EMBODIMENTS

The present invention will be described hereinafter with reference to FIGS. 6 to 19.

Figure 1:
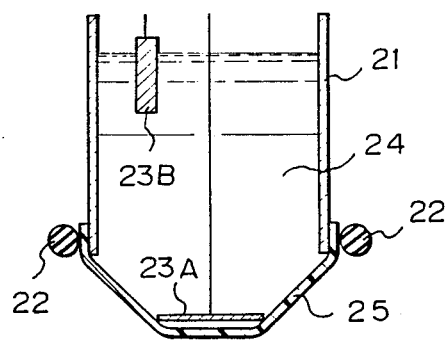
FIG. 1 is a cross-sectional view of the prior art oxygen electrode using a glass container.
Figure 2:
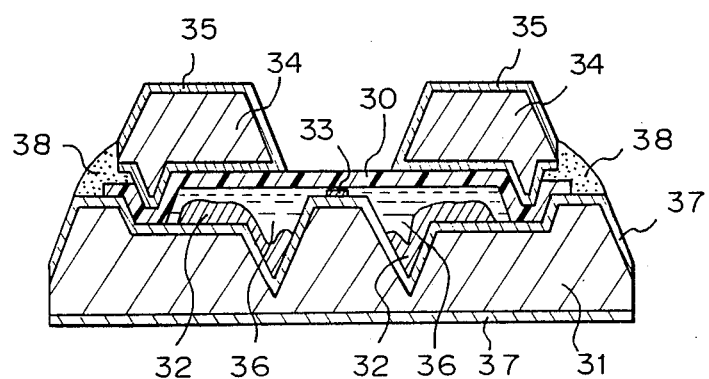
FIGS. 2 to 4 are cross-sectional views of the prior art miniaturized and integrated oxygen electrodes.
Figure 3:
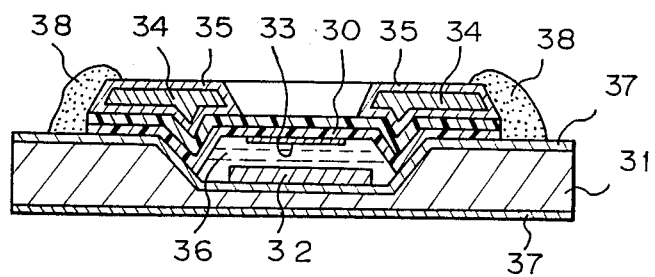
Figure 4:
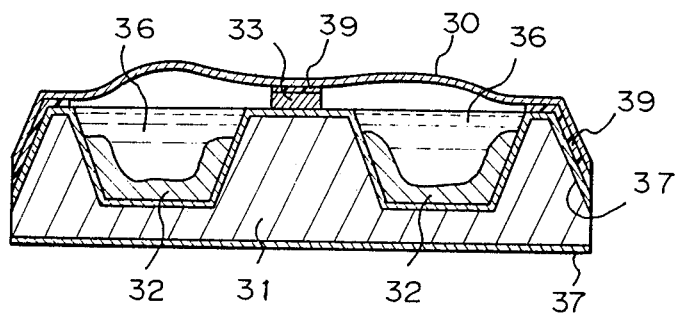
Figure 5:
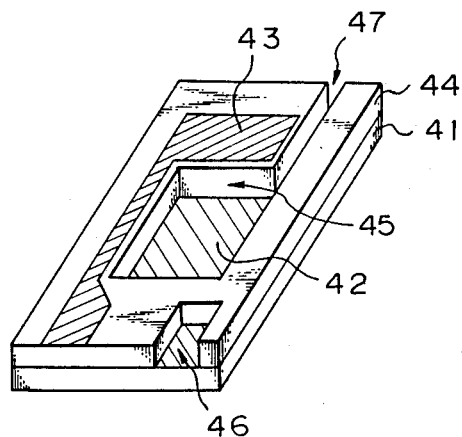
FIG. 5 is a perspective view of the prior art oxygen electrode fabricated without using a conventional anisotropic etching technology.
Figure 6:
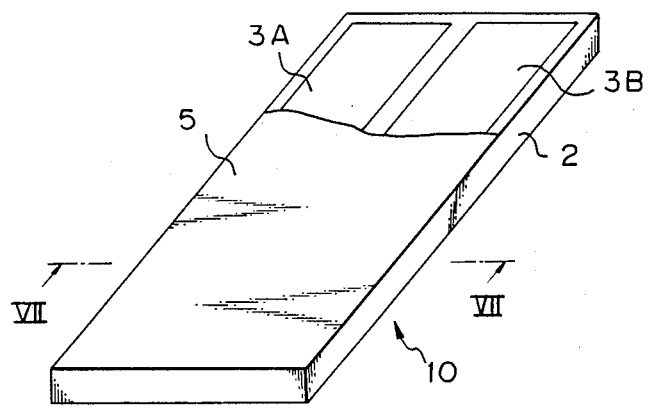
FIG. 6 is a perspective view of the miniaturized and integrated oxygen electrode according to the present invention.

FIG. 6 is a perspective view showing a preferred embodiment of the miniaturized oxygen electrodes (micro-oxygen electrodes) according to the present invention. As illustrated, a micro-oxygen electrode 10 has a rectangular configuration and contains two electrodes 3A and 3B on a silicon oxide ($SiO_2$) insulating layer 2. The electrode 10 is a polarographic oxygen electrode and, therefore, the electrodes 3A and 3B are made of gold. Reference number 5 is an oxygen gas-permeable membrane covering a sensing portion of the oxygen electrode.

Figure 7:
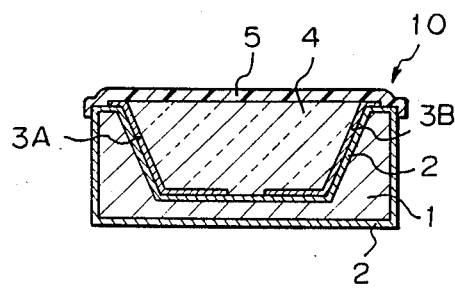
FIG. 7 is a cross-sectional view of the oxygen electrode taken along the line VII–VII of FIG. 6.

The structure of the micro-oxygen electrode of FIG. 6 is clear from FIG. 7 showing the sensing portion of the electrode taken along the line VII—VII of FIG. 6. A silicon (Si) substrate 1 has an insulating layer $SiO_2$ layer 2 formed on an overall surface thereof in addition to a recess-groove formed by anisotropic etching. The recess in this instance is in the form of an inverted trapezoid, but any other configuration is acceptable. The inverted trapezoid-shaped recess has a pair of Au electrodes 3A and 3B deposited on an inner surface thereof. The recess is filled with an electrolyte solution-carrying material (gel) 4, and an upper surface thereof is covered with the oxygen gas-permeable membrane 5.

Figure 8:
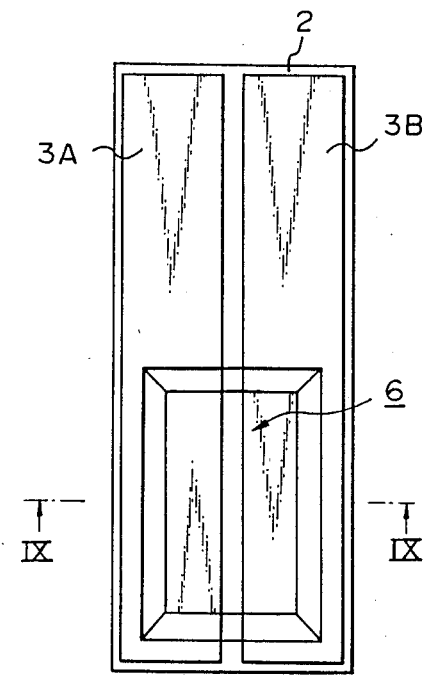
FIG. 8 is a plan view of the electrode body used in the oxygen electrode of FIG. 6.
Figure 9:
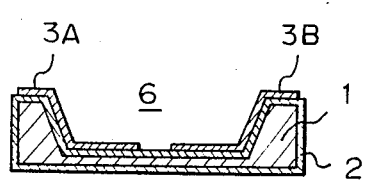
FIG. 9 is a cross-sectional view of the electrode body taken along the line IX–IX of FIG. 8.

The body of the micro-oxygen electrode is further illustrated in FIG. 8 and FIG. 9, which is a cross-sectional view taken along the line IX—IX of FIG. 8. The inverted trapezoid-shaped recess described above is indicated by the reference number 6. Both of the Au electrodes 3A and 3B extend to the inner surface of the recess 6. The length, width and thickness of this electrode body are 15 mm, 4 mm, and 350 μm, respectively. Narrower electrodes such as those having a width of 1 mm, 2 mm or 3 mm can be similarly produced.

In the illustrated polarographic micro-oxygen electrode, an application of a predetermined voltage (for example, 0.8 volts) between the two Au electrodes 3A and 3B will result in the following reduction reaction at a surface of either of the Au cathodes 3A or 3B.

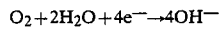

$$O_2 + 2H_2O + 4e^- \rightarrow 4OH^-$$

Due to the reduction of oxygen, electrons are discharged from the cathode to the oxygen, and thus an electric current is generated. As apparent from the above reaction, the resulting electric current is proportional to the concentration of oxygen. Accordingly, the concentration of oxygen can be quantitatively determined using the electric current as an index.

The micro-oxygen electrode of FIGS. 6 and 7 can be produced in accordance with a series of fabrication steps shown, for example, in FIGS. 10A to 10K. In these figures, the production of only one oxygen electrode is illustrated in sequence, to simplify understanding of the fabrication steps, but it should be noted that, in practice, numerous micro-oxygen electrodes can be concurrently fabricated on a single wafer or silicon substrate.

1. Wafer washing (FIG. 10A):

A <100> oriented p-type silicon wafer having a diameter of 2 inches and a thickness of 350 $\mu$m is prepared. The Si wafer 1 is washed successively with an aqueous mixed solution of hydrogen peroxide and ammonia, and concentrated nitric acid.

2. Formation of $SiO_2$ layer (FIG. 10B):

The Si wafer 1 is subjected to a conventional thermal oxidation in a wet state to form an $SiO_2$ layer 2, which acts as an electrically insulating layer, on an overall surface of the wafer 1. The $SiO_2$ layer thus obtained has a thickness of about 1.0 to 1.2 $\mu$m.

3. Application of resist pattern (FIG. 10C):

Before anisotropic etching, the Si wafer 1 is covered with a desired pattern 7 of the negative-working photoresist (OMR-83, commercially available from Tokyo Oka Co.). The resist pattern 7 is used as a mask in the subsequent step of selective etching of the underlying $SiO_2$ layer 2.

4. Formation of resist coating (FIG. 10D):

A lower surface of the Si wafer 1 not having the resist pattern is coated with the negative-working photoresist, which is identical to that used in the above patterning step. The wafer 1 is baked at 120° C. for 1 hour, and thus the resist coating 8 is formed.

Figure 10A:
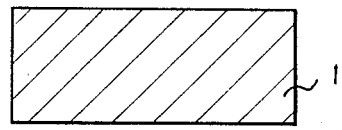
FIGS. 10A to 10K are cross-sectional views illustrating, in sequence, the production of the oxygen electrode of FIG. 6.
Figure 10B:
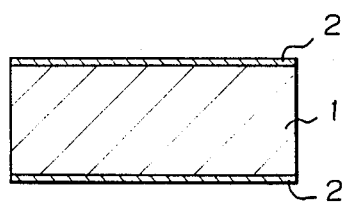
Figure 10C:
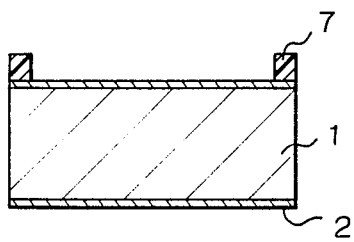
Figure 10D:
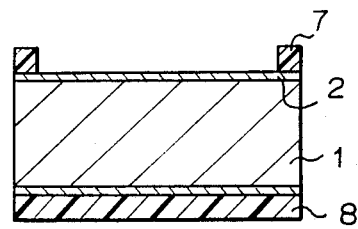
Figure 10E:
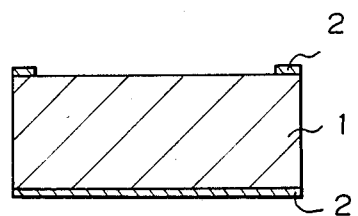
Figure 10F:
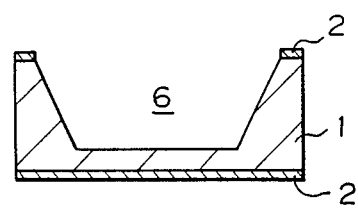
Figure 10G:
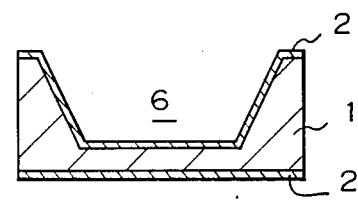
Figure 10:
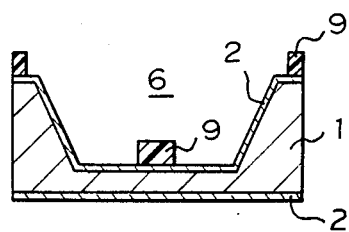
Figure 10:
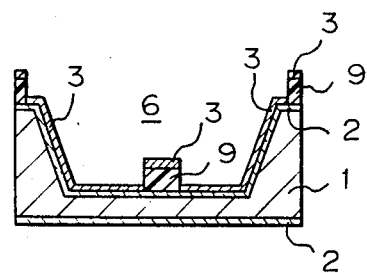
Figure 10:
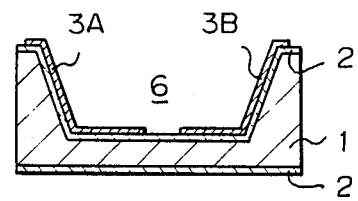
Figure 10:
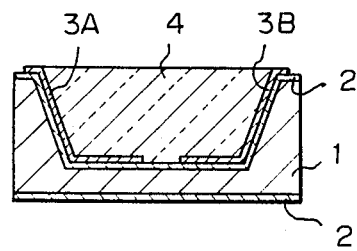
Figure 11:
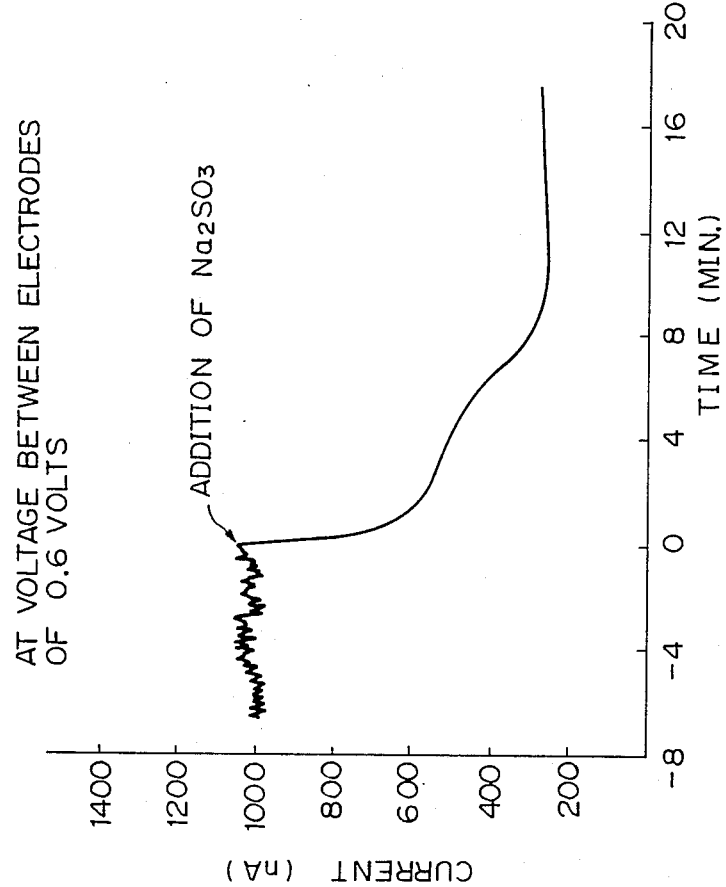
FIG. 11 is a graph showing a typical response curve for the oxygen electrode according to the present invention.
Figure 12:
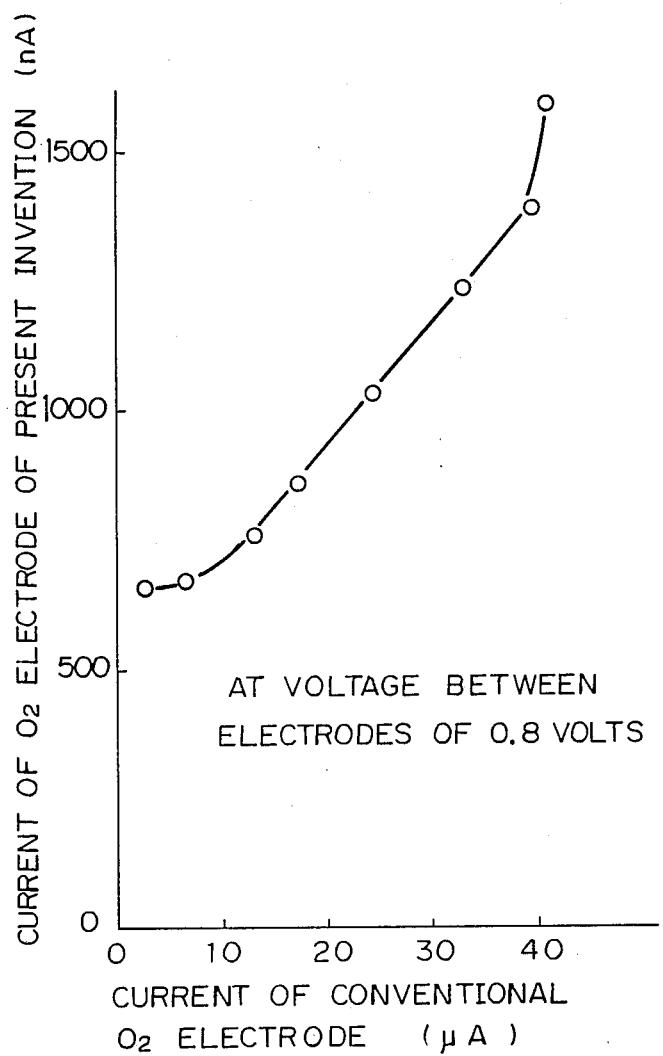
FIG. 12 is a graph comparing the response of the oxygen electrode of the present invention with that of a conventional oxygen electrode.

5. Formation of window (FIG. 10E):

A window for anisotropic etching is opened in the $SiO_2$ layer 2 of the Si wafer 1. This window formation is performed by dipping the wafer 1 in an aqueous solution of 50% hydrofluoric acid 50% ammonium fluoride (1:6), to etch off the unmasked $SiO_2$ layer, i.e., the $SiO_2$ layer 2 not having the resist pattern 7 (see FIG. 10D). After the etching is completed, the remaining resist is removed in a solution of sulfuric acid and hydrogen peroxide (2:1) at room temperature. As shown in FIG. 10E, the window is formed in the $SiO_2$ layer 2. Thus the Si wafer 1 is exposed in an area in which anisotropic etching is carried out in the next step.

6. Anisotropic etching of Si wafer (FIG. 10F):

The Si wafer 1 is anisotropically etched in an aqueous solution of 35% potassium hydroxide at 80° C. The remaining $SiO_2$ layer 2 on the upper surface of the wafer 1 is used as a mask in this step. After etching, the wafer 1 is washed with distilled water. Thus, a recess or groove 6 in the form of inverted trapezoid is formed.

7. Formation of $SiO_2$ layer (FIG. 10G):

First, the $SiO_2$ layer 2 used as the mask in the above step is removed with the same solution as used in step (5). After washing, the wafer 1 is subjected to a conventional wet thermal oxidation at 1000° C., and thus a newly grown $SiO_2$ layer 2 having a thickness of 5000 Å is formed on the upper surface of the wafer 1.

8. Application of resist pattern (FIG. 10H):

As a mask to be used in the process of the electrode formation, a pattern of the negative-working photoresist 9 is formed on the $SiO_2$ layer 2 of the Si wafer. The resist pattern 9 thus covers $SiO_2$ areas other than those on which electrodes are formed. The photoresist used is the same as used in step (3).

9. Deposition of electrode material (FIG. 10I):

As the first step in the electrode formation, gold 3 as an electrode material is vacuum deposited at a thickness of 1 $\mu$m on an overall surface of the Si wafer 1. Prior to this Au deposition, a chromium layer 500 Å thick (not shown) is deposited to improve the adhesion of the Au layer 3 to the $SiO_2$ layer 2.

10. Formation of electrodes (FIG. 10J):

After deposition of the electrode material, the mask used, namely, the resist pattern, is removed in warm sulfuric acid, and electrodes 3A and 3B of gold are thus formed. The cross-sectional view of FIG. 10J corresponds to that of FIG. 9.

11. Formation of electrolyte solution-carrying gel (FIG. 10K):

An electrolyte solution-carrying gel 4 is filled in the inverted trapezoid-shaped recess of the Si wafer 1. First, agarose is dissolved in an aqueous solution of 0.1 M KCl, the solution is added to the recess after heating, using a micro-syringe, and the agarose solution is left to stand. The agarose is then cooled and solidified to form a gel, and thus the electrolyte solution-containing gel 4 is produced.

12. Formation of gas-permeable membrane

Finally, a silicone resin (SR2410, commercially available from Toray Silicone Co.) is coated on an overall surface of the Si wafer 1. The oxygen gas-permeable membrane consisting of silicone resin will strongly adhere to the wafer 1. Thus, a desired micro-oxygen electrode 10 illustrated in FIGS. 6 and 7 is obtained.

As an alternative, negative-working photoresists such as those used as the pattern forming material in the above-described steps (3) and (8) can be advantageously utilized as the oxygen gas-permeable membrane, since they have a good oxygen gas permeability and exhibit an excellent mechanical and adhesive strength in addition to an ease of coating. For example, the negative photoresist: OMR-83 is spin-coated to a thickness of 3 $\mu$m on the Si wafer, followed by exposure to UV rays. The photoresist coating capable of functioning as the gas-permeable membrane can be obtained at a relatively low spinning speed, for example, less than 3,000 rpm, but a spinning speed of about 1,500 to 2,000 rpm is preferred because the resulting coating is homogeneous and has a uniform thickness.

Using the micro-oxygen electrode produced in accordance with the above fabrication steps and using the photoresist OMR-83 as the gas-permeable membrane, a response characteristic of the micro-oxygen electrode is determined and plotted as a graph of response time vs. electric current. A voltage of 0.6 volts is applied between the Au electrodes. In order to measure a response time of the micro-oxygen electrode when the concentration of oxygen is changed from saturation to almost zero, a sensing portion of the electrode is dipped into a buffer solution of phosphoric acid having a pH of 7, followed by an addition of sodium sulfite ($Na_2SO_3$) to reduce the concentration of oxygen dissolved in the buffer solution. The results are plotted in FIG. 11, from which it can be seen that the electrode responded as soon as $Na_2SO_3$ was added to the buffer solution, and stabilized about 8 minutes later.

In addition, a comparison is made of the response characteristics of the micro-oxygen electrode of the present invention and a conventional galvanic oxygen electrode. Both electrodes are dipped in a buffer solution of phosphoric acid having a pH of 7 and their response characteristics determined after $Na_2SO_3$ is added to the solution to change the concentration of the dissolved oxygen. The voltage applied between the electrodes is 0.8 volts. The results of comparison are plotted as a graph of the current of the conventional oxygen electrode vs. that of the micro-oxygen electrode of the present invention, in FIG. 12. The results of FIG. 12 indicate that there is a linear relationship between the responses of these two oxygen electrodes, and that the micro-oxygen electrode of the present invention is more sensitive to the change of the concentration of the dissolved oxygen.

The micro-oxygen electrodes according to the present invention have many advantages derived from their structures and production processes. The sizes and characteristics of the resulting micro-oxygen electrodes are uniform because they are produced by a lithographic technique, and although they are very small in size, the fabrication accuracy thereof is high. In addition, the electrodes can be produced by a mass-production process and, therefore, the costs thereof are notably reduced. This reduction of costs means that the electrodes can be disposed of after use, although they can be repeatedly used if desired. Further, because an electrolyte solution-containing gel is used in the recess, the electrolyte solution is easily added to the recess and to the recess easily covered with the gas-permeable membrane. Furthermore, the electrodes can be used for in vivo measurements.

The miniaturized oxygen electrodes of the present invention can be used in various fields. For example, they can be advantageously used as a transducer in the production of a miniaturized biosensor which comprises a receptor having biological substances immobilized in an organic medium and a transducer. As previously described, the biosensors can be utilized in chemical analysis, industrial process and environmental conditioning, for example.

Figure 13:
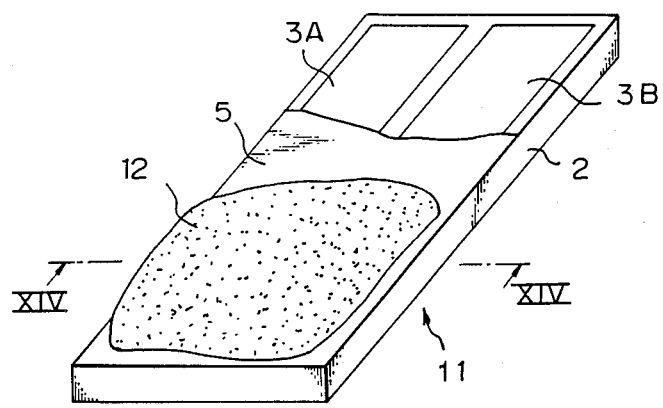
FIG. 13 is a perspective view of the miniaturized and integrated biosensor according to the present invention.
Figure 14:
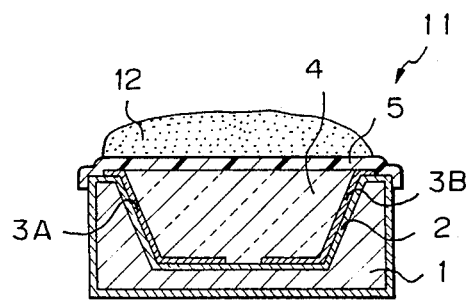
FIG. 14 is a cross-sectional view of the biosensor taken along the line XIV-XIV of FIG. 13.

FIG. 13 is a perspective view showing a preferred embodiment of the miniaturized biosensors according to the present invention. The illustrated microbiosensor 11 is a glucose microsensor and, as shown in FIG. 14, which is a cross-section along the line XIV—XIV of FIG. 13, has an enzyme-immobilized membrane 12 on a sensitive portion of the micro-oxygen electrode of FIG. 6.

The microbiosensor of FIG. 13 is produced by forming a receptor on a sensitive portion of the micro-oxygen electrode after the micro-oxygen electrode is produced in accordance with the fabrication steps of FIGS. 10A to 10K. The receptor of the microsensor can be produced, for example, by dropping 20 μl of an aqueous solution of 10% bovine serum albumin (BSA), having 5 mg of glucose oxidase (GOD), dissolved therein on a sensitive portion of the micro-oxygen electrode. To induce a cross-linking reaction of the BSA and glutaraldehyde (GA), 10 μl of an aqueous solution of 25% GA is then added dropwise thereto. As an alternative, the sensitive portion of the electrode may be dipped in a mixed solution of 5 mg of GOD, 20 μl of a 10% BSA solution, and 10 μl of a 25% GA solution. The cross-linking reaction of BSA and GA then proceeds, and finally, as shown in FIG. 14, a GOD-immobilized membrane 12 is firmly adhered to the sensitive portion of the micro-oxygen sensor.

Figure 15:
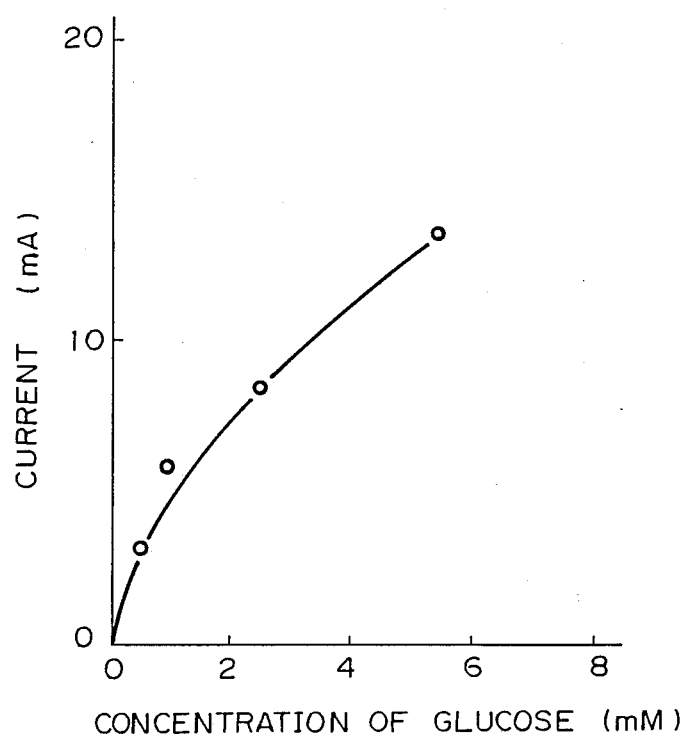
FIG. 15 is a calibration curve of the biosensor according to the present invention.

The glucose microsensor thus produced is then tested to determine the response characteristics thereof. A sensitive portion of the microsensor is immersed in a buffer solution of 0.1 M phosphoric acid (pH=7) at 27° C., and then a constant voltage of 0.6 volts is applied between two Au electrodes. After stabilization, a test solution containing glucose is added to the buffer solution. Glucose is oxidized with the GOD immobilized on the sensitive portion of the microsensor, and concurrently, oxygen around the micro-oxygen electrode is consumed. Since the oxygen concentration varies, an electric current passed through the electrodes also changes. Based on such a change of electric current, a concentration of glucose can be determined. FIG. 15 shows a calibration curve of the glucose microsensor, and indicates that the microsensor can respond substantially linearly over a wide range of glucose concentration. This is comparable to conventional glucose sensors.

According to the present invention, amperometric and miniaturized glucose biosensors and other biosensors can be produced with a high fabrication accuracy and by a mass-production process, and can be used for in vivo monitoring, for example, by inserting the sensor into a small space such as catheter. Since the production costs are remarkably reduced, the sensors may be used as disposable products, if desired.

The micro-oxygen electrodes according to the present invention can be produced in the manner described above with reference to FIGS. 10A to 10K. Alternatively, they can be produced as follows.

FIGS. 16A to 16F illustrate, in sequence, the production of the micro-oxygen electrode containing an electrolyte solution-carrying polymeric gel. This production process is particularly suited to the mass-production of the electrodes with a low cost. The fabrication steps comprise:

1. Formation of electrodes (FIG. 16A):
   Gold electrodes 3A and 3B are deposited on an $SiO_2$ coating 2 on the Si wafer 1 in the same manner as described with reference to FIG. 10J. The preceding steps (not shown) correspond to those of FIGS. 10A to 10I.

Figure 16A:
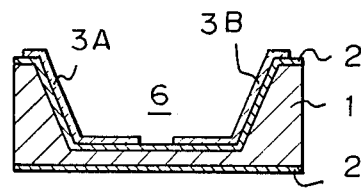
FIGS. 16A to 16F are cross-sectional views illustrating, in sequence, the production of the oxygen electrode according to the present invention.
Figure 16B:
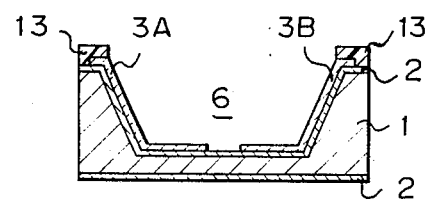

2. Coating of photoresist (FIG. 16B):
   After formation of the electrodes 3A and 3B, the Si wafer 1 is spin coated with the negative-working photoresist (OMR-83) to wholly cover the wafer 1. The photoresist coating 13 is then prebaked, exposed and developed. As shown in FIG. 16B, the photoresist coating 13 covers the overall surface of the wafer 1 except for the recess portion 6.

3. Dipping in gel-forming solution (FIG. 16C):
   An electrolyte solution-carrying polymeric gel is produced by polymerizing the corresponding photopolymerizable monomers. The following four solutions are prepared for this purpose.
   Solution A:
      30 g of acrylamide (photopolymerizable monomer) and 0.8 g of N,N'-methylene bis acrylamide (cross-linking agent) are dissolved in an aqueous solution of 0.1 M KCl to produce 100 ml.
   Solution B:

4 mg of riboflavin (vitamin $B_2$, hardening accelerator) is dissolved in an aqueous solution of 0.1 M KCl to produce 100 ml.

Solution C:
0.46 ml of N,N,N',N'-tetramethyl ethylenediamine (polymerization initiator) is dissolved in an aqueous solution of 0.1 M KCl to produce 100 ml.

Solution D:
An aqueous solution of 0.1 M KCl.

These solutions A, B, C, and D are separately prepared to avoid undesirable polymerization occurring if they are mixed and stored.

Just before use, these solutions are mixed in a ratio of Solution A : Solution B : Solution C : Solution D = 2:1:1:4 to obtain an aqueous solution of monomers capable of forming an electrolyte solution-carrying polymeric gel. The resist-coated Si wafer 1 produced in the step of FIG. 16B is then dipped in this aqueous solution 14 of acrylamide-containing KCl as the electrolyte.

4. Polymerization of monomers (FIG. 16D):

After a predetermined time, the wafer 1 is removed from the aqueous solution 14 of acrylamide. The aqueous solution 14 remains only in the recess, because the photoresist 13 is hydrophobic and repels the aqueous solution. The wafer 1 is then exposed to radiations 15 generated from a mercury vapor lamp or fluorescent lamp (not shown) to induce polymerization of the acrylamide in the solution 14, and polymerization proceeds accordingly.

5. Formation of electrolyte solution-carrying gel (FIG. 16E):

As a result of the polymerization of the acrylamide, an electrolyte solution-carrying polymeric gel 16, namely, a porous polyacrylamide having an aqueous solution of KCl impregnated in the pores thereof, is obtained.

6. Formation of gas-permeable membrane (FIG. 16F):

The negative-working photoresist (OMR-83) used in the step of FIG. 16B is again used herein, but as an oxygen gas-permeable membrane, since the resulting coating can exhibit a satisfactory oxygen gas permeability, mechanical strength, and adhesion to the electrolyte-carrying gel. The photoresist pattern used as the mask in the previous step is not removed, since it has no adverse effect on this gas-permeable membrane. The photoresist (OMR-83) is spun coated to a thickness of about 2 μm on the wafer 1 and is immediately exposed without prebaking to form a gas-permeable membrane 13. The thinner in the resulting resist or membrane is removed by dipping the wafer in purified water or standing in an atmosphere saturated with water vapour for one day and night.

In addition, to prevent undesirable evaporation of the electrolyte solution during gelation due to an increase of a ratio of the surface area to the volume of the recess in the wafer, the micro-oxygen electrodes can be produced in the sequence shown in FIGS. 17A to 17F. FIGS. 17A to 17F each correspond to FIGS. 16A to 16F previously explained.

1. Formation of electrodes (FIG. 17A):

The Au electrodes 3A and 3B are deposited on an $SiO_2$ coating 2 of the Si wafer 1 in the same manner as described with reference to FIG. 10J. The preceding steps (not shown) correspond to those of FIGS. 10A to 10I.

Figure 17A:
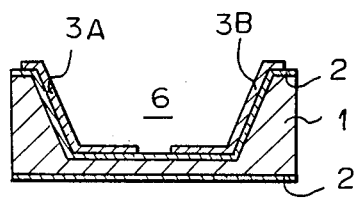
FIGS. 17A to 17F are cross-sectional views illustrating, in sequence, the production of the oxygen electrode according to the present invention.
Figure 17B:
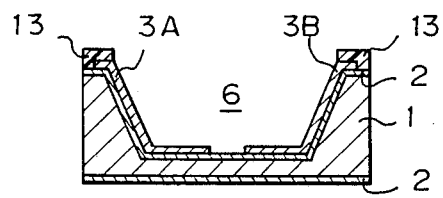
Figure 17C:
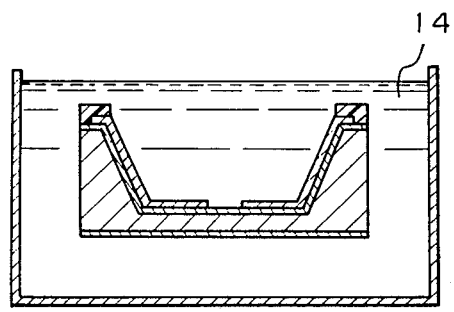
Figure 17D:
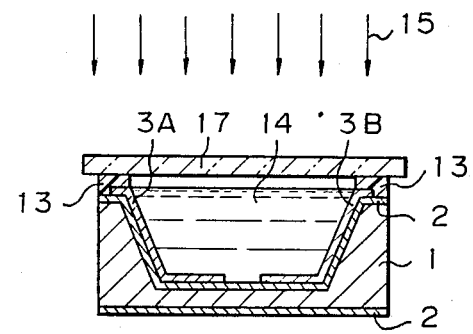
Figure 17E:
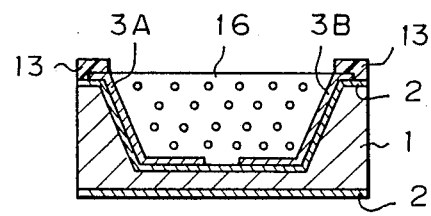
Figure 17F:
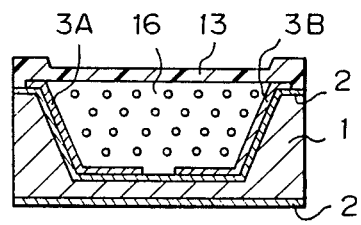

2. Coating of photoresist (FIG. 17B):

After formation of the electrodes 3A and 3B, the Si wafer 1 is spin coated with the negative-working photoresist (OMR-83) the wholly cover the wafer 1. The photoresist coating 13 is then prebaked, exposed and developed. As shown in FIG. 17B, the photoresist coating 13 covers the overall surface of the wafer 1 except for the recess portion 6.

Figure 16C:
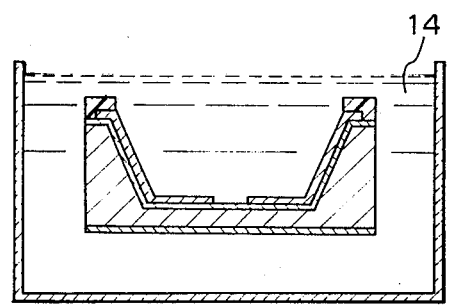
Figure 16D:
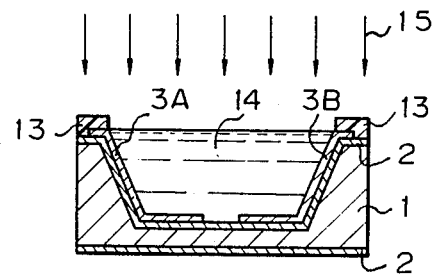
Figure 16E:
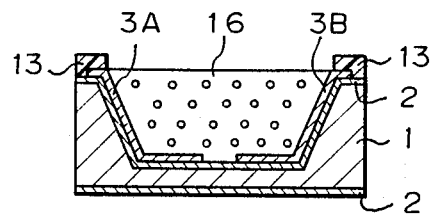
Figure 16F:
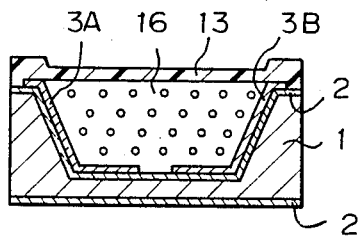

3. Dipping in gel-forming solution (FIG. 17C):

An electrolyte solution-carrying polymeric gel is produced, as in FIG. 16C, by polymerizing the corresponding photopolymerizable monomers. The following four solutions are prepared for this purpose.

Solution A:
30 g of acrylamide (photopolymerizable monomer and 0.8 g of N,N'-methylene bis acrylamide (cross-linking agent) are dissolved in an aqueous solution of 0.1 M $Na_2SO_4$ to produce 100 ml.

Solution B:
4 mg of riboflavin (vitamin $B_2$, hardening accelerator) is dissolved in an aqueous solution of 0.1 M Na to produce 100 ml.

Solution C:
0.23 g of N,N,N',N'-tetramethyl ethylenediamine (polymerization initiator) is dissolved in an aqueous solution of 0.1 M $NaSO_4$ to produce 100 ml.

Solution D:
An aqueous solution of 0.1 M $Na_2SO_4$.

These solutions A, B, C, and D are separately prepared to avoid undesirable polymerization occurring if they are mixed and stored.

Just before use, these solutions are mixed in a ratio of Solution A : Solution B : Solution C : Solution D = 4:1:1:1 to obtain an aqueous solution of monomers capable of forming an electrolyte solution-carrying polymeric gel. The resist-coated Si wafer 1 produced in the step of FIG. 17B is then dipped in this aqueous solution 14 of acrylamide containing $Na_2SO_4$ as the electrolyte.

4. Polymerization of monomers (FIG. 17D):

After a predetermined time, the wafer 1 is removed from the aqueous solution 14 of acrylamide. The aqueous solution 14 remains only in the recess, because the photoresist 13 is hydrophobic and repels the aqueous solution. The wafer 1 is then immediately covered with a transparent cover glass 17 0.1 mm thick. The cover glass 17 used effectively prevents evaporation of the electrolyte solution, and in particular, the water content thereof, from the recess of the wafer 1. Thereafter, the wafer 1 is exposed to radiations 15 generated from a mercury vapor lamp or fluorescent lamp (not shown) to induce polymerization of the acrylamide in the solution 14, and polymerization proceeds accordingly.

5. Formation of electrolyte solution-carrying gel (FIG. 17E):

As a result of the polymerization of the acrylamide, an electrolyte solution-carrying polymeric gel 16, namely, a porous polyacrylamide having an aqueous solution of $Na_2SO_4$ impregnated in pores thereof, is obtained.

6. Formation of gas-permeable membrane (FIG. 17F):

The negative-working photoresist (OMR-83) used in the step of FIG. 17B is again used, but as an oxygen gas-permeable membrane, since the resulting coating exhibits a satisfactory oxygen gas permeability, mechanical strength, and adhesion to the electrolyte-carrying gel. The photoresist pattern used as the mask in the previous step is not removed, since it has no adverse effect on this gas-permeable membrane. The photoresist (OMR-83) is spin coated to a thickness of about 2 μm on the wafer 1 and is immediately exposed without prebaking to form a gas-permeable membrane 13. The thinner in the resulting resist or membrane is removed by dipping the wafer in purified water or standing in an atmosphere saturated with water vapor for one day and night.

According to the production method described above with reference to FIGS. 17A to 17F, electrolyte solution-carrying polymeric gels having a uniform volume, small size and flat surface can be easily produced. The formation of a gas-permeable membrane on the surface of the gel also can be easily attained. The characteristics of the micro-oxygen electrodes produced are remarkably uniform.

In addition, the micro-oxygen electrodes according to the present invention can be produced by using a "sol-gel method" in the formation of the electrolyte solution-containing gel. The production process is particularly suited to the mass-production of the micro-oxygen electrodes for use in in vivo measurements, because the materials used in the electrolyte-carrying gel have no toxicity to the human body.

In this production process of the micro-oxygen electrodes, as a porous carrier material in the pores of which the electrolyte solution is supported, a gel which is obtained in the process of glass production according to the sol-gel method is used. This gel is considered appropriate since it is relatively hard and contains a sufficient amount of water.

Metal alkoxide used as a starting material in the sol-gel method can be represented by the formula:

$Me(OR)_n$ in which Me is a metal, R is an alkyl group such as methyl and ethyl, and n is an integer. One example of this metal alkoxide is tetraethoxysilane $Si(OC_2H_5)_4$. Using the metal alkoxide as the starting material, the sol-gel method can be carried out in the manner outlined in the flow sheet of FIG. 19. The metal alkoxide is hydrolyzed and then polycondensated, and surprisingly, in this method, the change in volume of the gel before and after gelation is negligible. Thus, gelation can be easily carried out with good results.

Based on the sol-gel method, the micro-oxygen electrodes can be produced as follows:

1. Formation of electrodes (FIG. 18A):

The Au electrodes 3A and 3B are deposited on an $SiO_2$ layer 2 of the Si wafer 1. This and preceding steps can be carried out in the manner described above in detail with reference to FIGS. 16A and 17A, respectively.

2. Coating of photoresist (FIG. 18B):

After formation of the electrodes 3A and 3B, the Si wafer 1 is spin coated with the negative-working photoresist (OMR-83, viscosity 60 cp) to wholly cover the wafer 1. The photoresist coating 13 is then prebaked, exposed and developed. As is shown in FIG. 16B, the photoresist coating 13 covers the overall surface of the wafer 1 except for the recess portion 6.

Figure 18A:
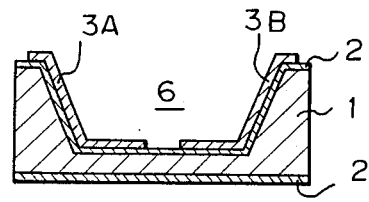
FIGS. 18A to 18F are cross-sectional views illustrating, in sequence, the production of the oxygen electrode according to the present invention; and, FIG. 19 is a flow sheet showing the production of glass from metal alkoxide in accordance with a conventional sol-gel process.
Figure 18B:
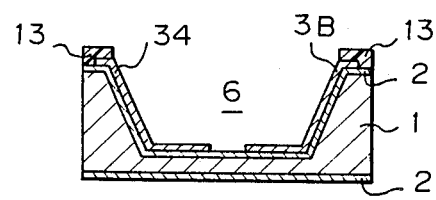
Figure 18C:
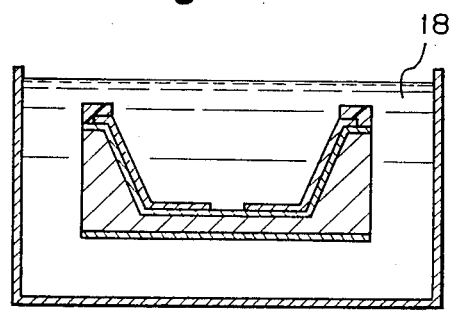
Figure 18D:
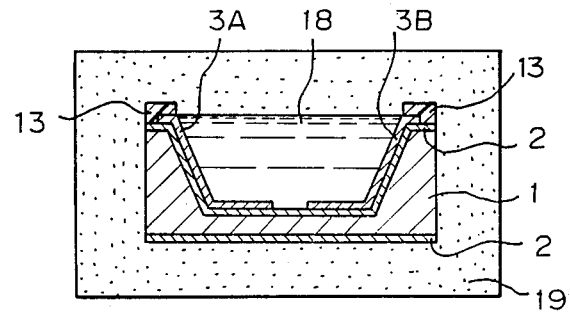
Figure 18E:
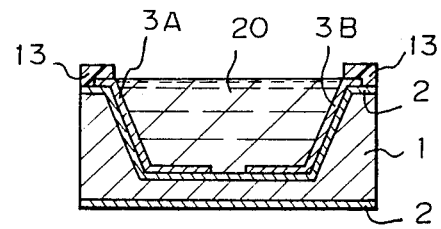
Figure 18F:
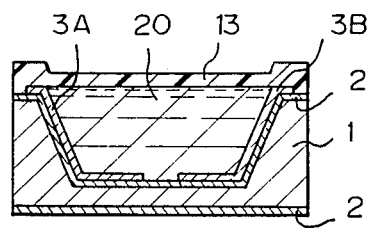
Figure 19:
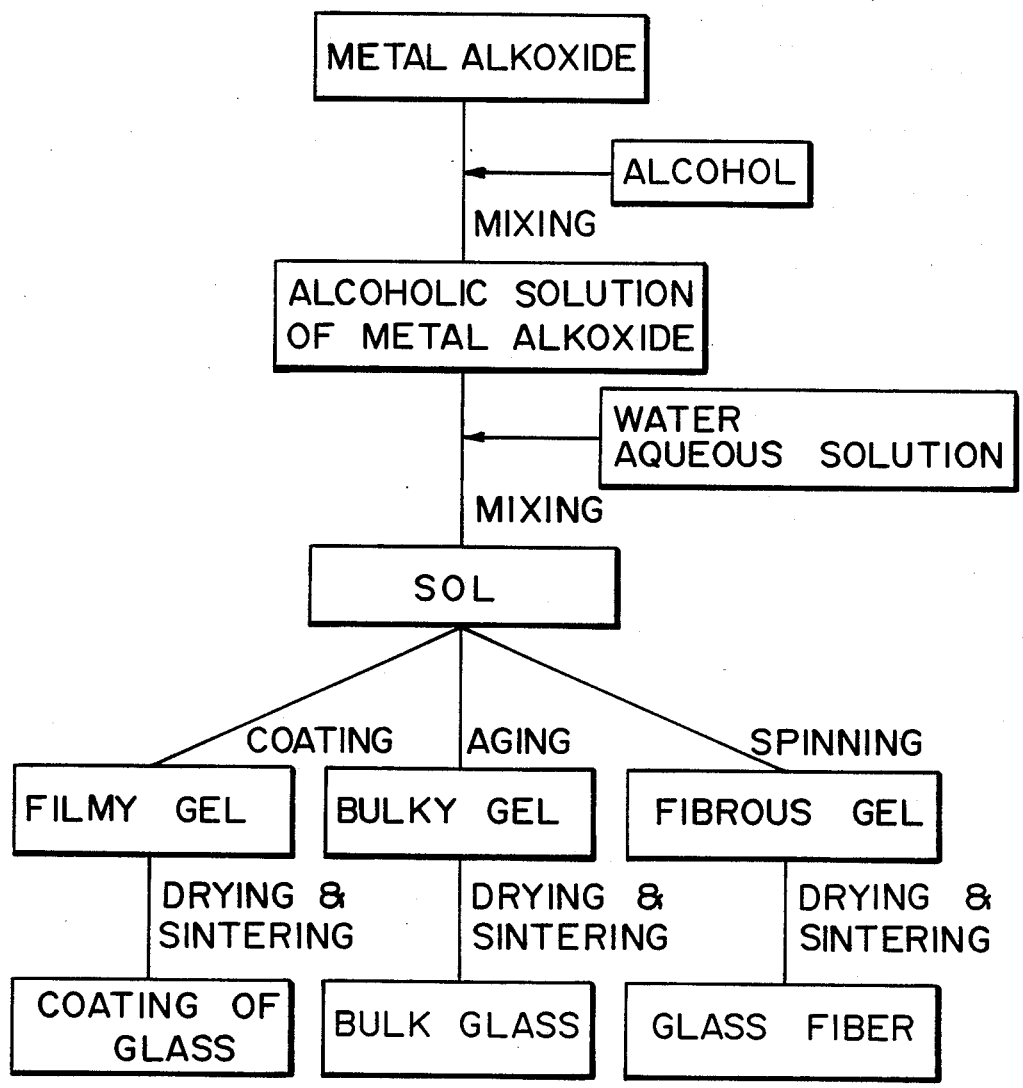

3. Dipping in gel-forming solution (FIG. 18C):

A mixed solution of tetraethoxysilane: ethanol:purified water (containing 0.15 M HCl and 0.1 M $Na_2SO_4$) in a molar ratio of 1:4:50 is thoroughly mixed at a room temperature by stirring. The resist-coated Si wafer 1 produced in the step of FIG. 18B is then dipped in this aqueous solution 18 containing $Na_2SO_4$ as the electrolyte.

4. Gelation of tetraethoxysilane (FIG. 18D):

After a predetermined time, the wafer 1 is removed from the aqueous solution 18. The solution 18 remains only in the recess, because the photoresist 13 is hydrophobic and repels the aqueous solution. The wafer 1 is subjected to the sol-gel process by leaving it to stand in an atmosphere saturated with water vapor 19 at 25° C. for 24 hours, and Gelation of tetraethoxysilane in the solution 18 proceeds gradually.

5. Formation of electrolyte solution-carrying gel (FIG. 18E):

As a result of the gelation of tetraethoxysilane, an electrolyte solution-carrying gel 20, namely, a porous gel having an aqueous solution of $Na_2SO_4$ impregnated in pores thereof, is obtained.

6. Formation of gas-permeable membrane (FIG. 18F):

The negative-working photoresist (OMR-83) used in the step of FIG. 18B is again used, but as an oxygen gas-permeable membrane and at a different viscosity, since the resulting coating exhibits a satisfactory oxygen gas permeability, mechanical strength, and adhesion to the electrolyte-carrying gel. The photo-resist pattern used as the mask in the previous step is not removed, since it has no adverse effect on this gas-permeable membrane. The photoresist (OMR-83, viscosity 45 cp) is dip coated to a thickness of about 2 μm on the wafer 1 and is immediately exposed without prebaking to form a gas-permeable membrane 13. The thinner in the resulting resist or membrane is removed by dipping the wafer in purified water or standing in an atmosphere saturated with water vapour for one day and night.

The HCl used in the mixed solution in the step (3) is spontaneously removed from the gel during storing. However, immediate removal of the HCl is required, the wafer can be immersed in a solution of electrolyte such as 0.1 M $Na_2SO_4$ for about 24 hours after completion of the gelation. After immersion, excess electrolyte adhered on a surface of the wafer can be removed by spraying with $N_2$ gas. Thereafter, the gas-permeable membrane is formed as described in step (6).

We claim:

1. A miniaturized oxygen electrode comprising:

a semiconductor substrate having outer surfaces and at least one recess formed on one of the surfaces thereof by anisotropic etching for receiving an aqueous electrolyte solution, the substrate having an insulating layer on the surfaces thereof, the recess having a bottom area;

two electrodes including a cathode and an anode which are formed on the insulating layer on at least part of the outer surface of the substrate, each electrode being at least partially extended to the bottom area of the recess;

a solid or semi-solid, porous, aqueous electrolyte solution-containing material filling the recess; and an oxygen gas-permeable membrane covering and sealing the recess with the porous material therein.

2. The oxygen electrode according to claim 1, wherein the semiconductor substrate is a <100> oriented silicon substrate.

3. The oxygen electrode according to claim 2, wherein the insulating layer is a silicon oxide layer formed by oxidizing the silicon substrate.

4. The oxygen electrode according to claim 1, wherein the electrodes are formed by vacuum deposition of selected metals.

5. The oxygen electrode according to claim 1, wherein both the cathode and the anode are made of the same material and each is selected from a group consisting of gold and platinum, and the electrolyte solution in contact with the electrodes is an aqueous solution of potassium chloride.

6. The oxygen electrode according to claim 1, wherein the cathode is made of a material selected from the group consisting of gold and platinum and the anode is made of a material selected from the group consisting of silver/silver chloride, lead, and silver, and the electrolyte solution in contact with the electrodes is an aqueous solution of potassium chloride.

7. The oxygen electrode according to claim 1, wherein the cathode is made of a material selected from the group consisting of gold and platinum and the anode is made of lead, and the electrolyte solution in contact with the electrode is an aqueous solution of potassium hydroxide.

8. The oxygen electrode according to claim 1, wherein the cathode is made of a material selected from the group consisting of gold and platinum, and the anode is made of silver, and the electrolyte solution in contact with the electrodes is an aqueous solution of potassium hydroxide.

9. The oxygen electrode according to claim 1, wherein the porous material is an agarose gel having the electrolyte solution entrapped therein.

10. The oxygen electrode according to claim 1, wherein the porous material is a polymeric gel of photopolymerizable monomers having the electrolyte solution entrapped therein.

11. The oxygen electrode according to claim 10, wherein the photopolymerizable monomers include acrylamide.

12. The oxygen electrode according to claim 1, wherein the porous material is a gel of metal alkoxide having the electrolyte solution entrapped therein.

13. The oxygen electrode according to claim 1, wherein the oxygen gas-permeable membrane is a coating of silicone resin.

14. The oxygen electrode according to claim 1, wherein the oxygen gas-permeable membrane is a coating of photoresist material.

15. A process for the production of miniaturized oxygen electrodes which comprises the steps of:
forming at least one recess on a semiconductor substrate having outer surfaces by photolithographic and anixotropic etching, the recess having a bottom area,
forming an insulating layer on the surface of the substrate including the recess,
forming two electrodes on a surface of the insulating layer such that the electrodes are on at least part of the outer surfaces and are at least partially extended to the bottom area of the recess,
filling the recess with a solid or semi-solid, porous, aqueous electrolyte solution-containing material, and
covering and sealing the recess containing the porous material with an oxygen gas-permeable membrane.

16. The production process according to claim 15, wherein the substrate is silicon and the step of forming an insulating layer comprises oxidizing the silicon substrate.

17. The production process according to claim 15, wherein the electrodes forming step comprises vacuum deposition of electrode materials selected from the group consisting of gold, platinum, silver, silver/silver chloride and lead.

18. The production process according to claim 15, wherein the filling step comprises pouring a heated solution of agarose containing the electrolyte solution into the recess and leaving the heated solution to stand for a time sufficient to form an agarose gel having the electrolyte solution entrapped therein.

19. The production process according to claim 15, wherein the filling step comprises pouring a solution of photopolymerizable monomers containing the electrolyte solution into the recess and irradiating the solution with radiations capable of inducing polymerization of the monomers to form a polymeric gel having the electrolyte solution entrapped therein.

20. The production process according to claim 19, wherein the photopolymerizable monomers are acrylamide and the filling step includes irradiating the solution with UV rays to cause polymerization thereof.

21. The production process according to claim 15, further comprising, after formation of the electrodes, coating the surface of the substrate except for the recess portion with a hydrophobic photoresist material, dipping the masked substrate in an aqueous solution of photopolymerizable monomers containing the electrolyte solution, and exposing the substrate containing the aqueous solution of monomers in the recess to radiations capable of inducing polymerization of the monomers to form a polymeric gel having the electrolyte solution entrapped therein.

22. The production process according to claim 21, further comprising exposing the substrate to the radiations after covering and closing the recess formed thereon with an evaporation-preventing means which allows passage of the radiations.

23. The production process according to claim 22, wherein the photopolymerizable monomers are acrylamide and the exposing step comprising exposing the solution to UV rays to cause polymerization thereof.

24. The production process according to claim 22, in which the photopolymerizable monomers are acrylamide and the solution thereof is exposed to UV rays to cause polymerization thereof.

25. The production process according to claim 15, wherein the filling step comprises pouring a solution of metal alkoxide containing the electrolyte solution into the recess and subjecting the solution to a sol-gel process to form a gel of metal alkoxide having the electrolyte solution entrapped therein.

26. The production process according to claim 25, wherein the metal alkoxide is tetraethoxysilane.

27. The production process according to claim 15, further comprising, after formation of the electrodes, coating the surface of the substrate except for the recess portion with a hydrophobic photoresist material, dipping the masked substrate in an aqueous solution of metal alkoxide containing the electrolyte solution, and subjecting the substrate containing the aqueous solution of metal alkoxide in the recess to a sol-gel process to form a gel of metal alkoxide having the electrolyte solution entrapped therein.

28. The production process according to claim 27, wherein the metal alkoxide is tetraethoxysilane.

29. The production process according to claim 15, wherein the covering and sealing step comprises coating the porous material-containing recess with a silicon resin to form the oxygen gas-permeable membrane.

30. The production process according to claim 15, wherein the covering and sealing step comprises coating the porous material-containing recess with a photoresist material to form the oxygen gas-permeable membrane.

31. A miniaturized biosensor comprising:
- an oxygen electrode having a sensitive site and including a semiconductor substrate having at least one recess having a bottom area and being formed by anisotropic etching on a surface thereof for receiving an aqueous electrolyte solution, an insulating layer formed on the substrate, two electrodes which act as a cathode and an anode and are formed on the insulating layer on the surface of the substrate and each of which electrodes is at least partially on the surface and are extended to the bottom area of the recess, and a solid or semi-solid, porous, aqueous electrolyte solution-containing material filling the recess, an oxygen gas-permeable membrane covering and sealing the recess and porous material contained therein; and
- an immobilized biological substance capable of catalyzing the oxidation of biochemical organic compounds and being positioned on the sensitive site of the oxygen electrode.

32. The biosensor according to claim 31, wherein the biological substance is an enzyme.

33. The biosensor according to claim 31, wherein the biological substance is a microorganism.

34. The biosensor according to claim 31, wherein the biological substance is a mixture of at least two enzymes and microorganisms.

35. The biosensor according to claim 31, wherein the sensitive site is sensitive to glucose.

36. The biosensor according to claim 31, wherein the biological substance is a mixture of at least two enzymes.

* * * * *

UNITED STATES PATENT AND TRADEMARK OFFICE
CERTIFICATE OF CORRECTION

PATENT NO. : 4,975,175
DATED : December 4, 1990
INVENTOR(S) : Isao Karube et al.

It is certified that error appears in the above-identified patent and that said Letters Patent is hereby corrected as shown below:

Col. 5, line 57, after "TEFLON" insert --(trade name)--.

Col. 9, line 50, after "Thus" insert a comma.

Col. 14, line 22, change "Na" to --$Na_2SO_4$--.

Col. 18, lines 49-52, delete in their entirety.

Signed and Sealed this

Fourth Day of August, 1992

*Attest:*

DOUGLAS B. COMER

*Attesting Officer*     *Acting Commissioner of Patents and Trademarks*